United States Patent
Anderson et al.

(10) Patent No.: US 6,721,593 B2
(45) Date of Patent: Apr. 13, 2004

(54) APPARATUS FOR BODY SURFACE MAPPING

(76) Inventors: John McCune Anderson, 16 Torrange Road, Holywood, County Down (GB), BT18 0NG; James Allen, 10 Dunadry Road, Muckamore, County Antrim (GB), BT41 2RR (*) Notice: Subject to any disclaimer, the term of this patent is extended or adjusted under 35 U.S.C. 154(b) by 0 days.

(21) Appl. No.: 09/331,372
(22) PCT Filed: Dec. 18, 1997
(86) PCT No.: PCT/IB97/01631
§ 371 (c)(1),
(2), (4) Date: Oct. 28, 1999
(87) PCT Pub. No.: WO98/26712
PCT Pub. Date: Jun. 25, 1998

(65) Prior Publication Data
US 2002/0062087 A1 May 23, 2002

(30) Foreign Application Priority Data
Dec. 18, 1996 (IE) .............................................. S960904

(51) Int. Cl.[7] ............................................ A61B 5/0432
(52) U.S. Cl. ...................................... 600/523; 600/509
(58) Field of Search .................................. 600/508, 509, 600/519, 512–513, 523, 393

(56) References Cited

U.S. PATENT DOCUMENTS

| | | | |
|---|---|---|---|
| 4,947,857 A | | 8/1990 | Albert et al. |
| 4,974,598 A | | 12/1990 | John |
| 5,311,873 A | * | 5/1994 | Savard et al. ................ 128/898 |
| 5,419,337 A | * | 5/1995 | Dempsey et al. ........... 600/515 |
| 5,458,116 A | * | 10/1995 | Egler .......................... 600/523 |
| 5,483,968 A | * | 1/1996 | Adam et al. ................ 600/508 |
| 5,520,191 A | * | 5/1996 | Karlsson et al. ............ 600/523 |
| 5,803,084 A | * | 9/1998 | Olson ......................... 600/512 |

FOREIGN PATENT DOCUMENTS

WO    WO 92/07509    5/1992

OTHER PUBLICATIONS

Ramachandran et al., "Reconstruction of Out–of–Plane Cardiac Displacement Patterns as Observed on the Chest Wall During Various Phases of ECG by Capacitance Transducer," *IEEE Transactions on Biomedical Engineering* 38(4):383–385 (1991).

* cited by examiner

Primary Examiner—Kennedy Schaetzle
Assistant Examiner—Kristen Droesch
(74) Attorney, Agent, or Firm—Pillsbury Winthrop LLP (57) ABSTRACT

An apparatus for body surface mapping comprises a plurality of electrodes for attachment to spatially separate locations on a human torso with each electrode capable of detecting the electrical activity associated with a heartbeat and producing a corresponding voltage. The electrodes are sampled at a rate of 1 KHz during a cardiac cycle and sets of sampled values are produced and stored. Positional variations of the maximum and minimum sampled values over time are displayed as a projection of trajectories of the maximum and minimum sampled values in a three dimensional (x, y, t) space onto planes perpendicular to a plane containing the electrodes.

14 Claims, 6 Drawing Sheets

ANTERIOR POSTERIOR

— MAXIMUM
----- MINIMUM

APPARATUS FOR BODY SURFACE MAPPING

This application is a National Phase Application of PCT International Application No. PCT/IB97/01631, filed on Dec. 18, 1997, designating the United States, and which claims priority to Irish Patent Application No. S960904, filed Dec. 18, 1996.

This invention relates to an apparatus for body surface mapping, for use in diagnosing different conditions of the human myocardium.

FIELD OF THE INVENTION

There are various methods which present the information contained in an ECG to the cardiologist, the most successful of which has been the standard twelve lead ECG. Unfortunately the standard ECG, in many instances, fails to provide an unequivocal diagnosis.

Figure 1:
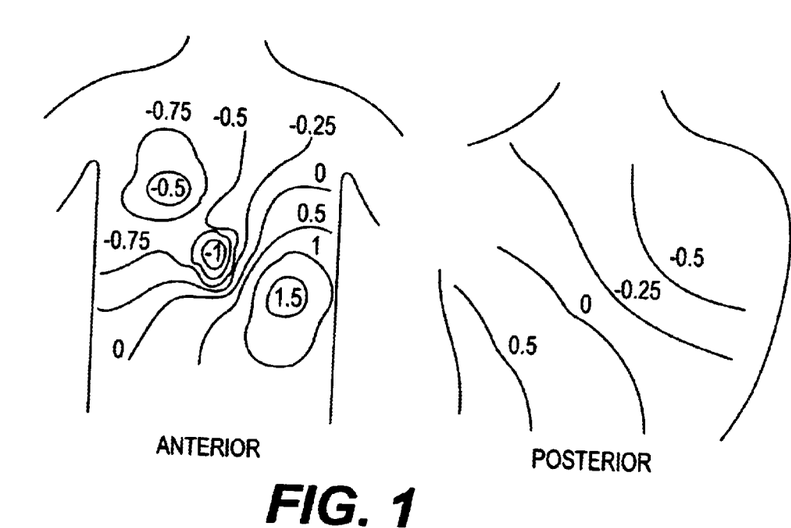
FIG. 1 is an isopotential map of a normal healthy subject mid-way through the heart's QRS (depolarization) period.

Even before the conventional twelve lead ECG became a medical standard, electrocardiographic body surface mapping (BSM) was being investigated as a method which increased spatial resolution and thereby increased diagnostic capability. These "maps" were viewed as pictures presenting lines joining areas of the same electrical potential (isopotentials) at a specified instant of time. This is shown in FIG. 1, which is an isopotential map of a normal healthy subject mid-way through the heart's QRS (depolarization) period. In FIG. 1 the map has been superimposed onto the outline of a human torso and is obtained from multiple ECG electrodes located substantially fully around the torso from the anterior (left hand side of FIG. 1) to the posterior (right hand side of FIG. 1).

Figure 2:
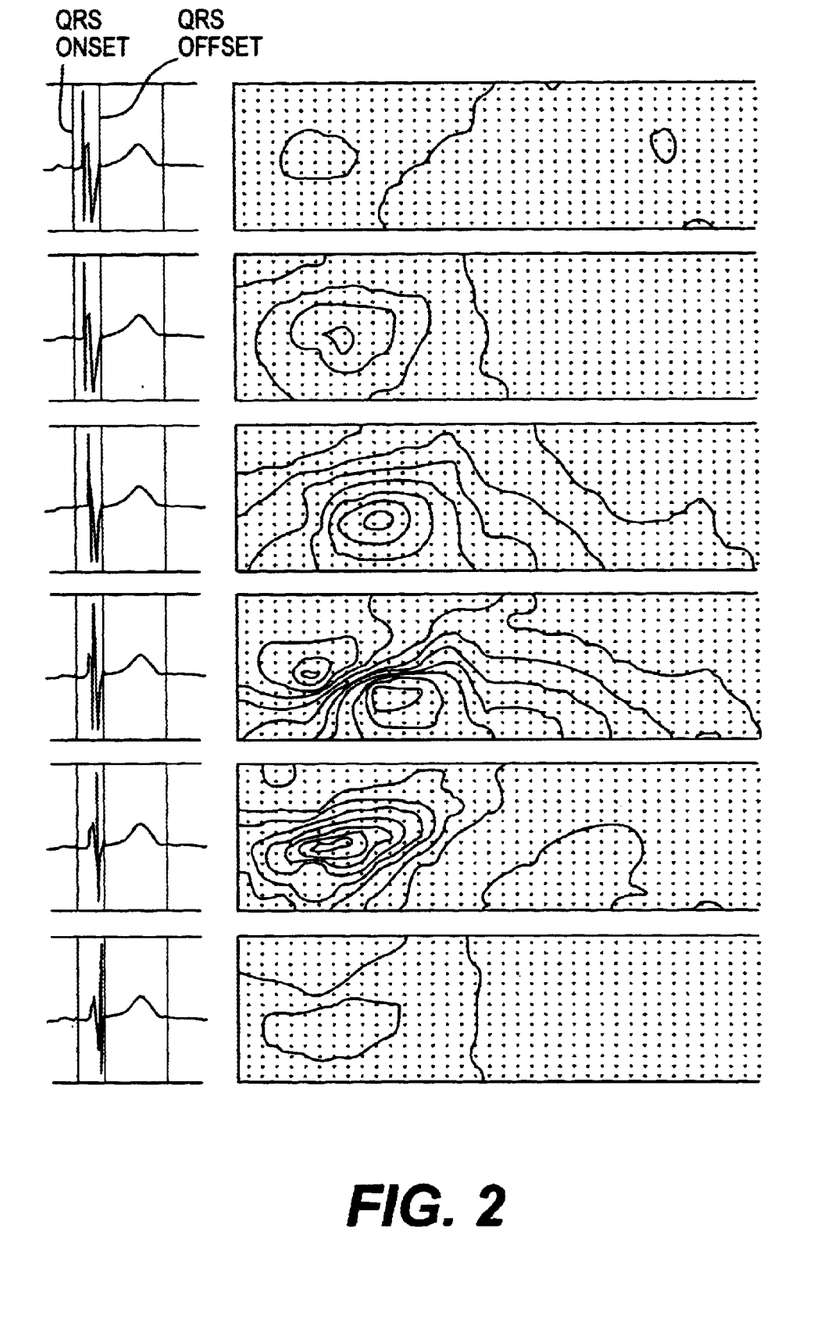
FIG. 2 illustrates six body surface isopotential maps showing how map morphology changes with time during the QRS period.

Since each map shows the isopotentials at only a single point in time, to see the whole electrical "picture" requires the viewing of successive maps at successive time instants throughout at least part of the cardiac cycle. Furthermore viewing these maps their pattern and morphology to be considered from one instantaneous map to the next. Thus, for example, FIG. 2 illustrates six body surface isopotential maps showing how map morphology changes with time during the QRS period, the ECGs on the left of FIG. 2 showing the successive points in time during the QRS period that the maps represent. Since the body is cylindrical in shape the maps actually represent the body "unwrapped" onto a two dimensional plane (see FIG. 1). It is conceivable, however, that such maps could be produced which do not "unwrap" the torso.

However, BSM is difficult to use and as a result much research has been carried out which attempts to bring the benefits of BSM in a fast easy to use form. Methods were introduced of portraying BSM information as mathematical integrations of the individual ECG waveforms. Isointegral maps present the body surface as lines which join areas possessing the same integral values of pre-defined sections of the ECG. Such isointegral maps have shown that there is more information outside the spatial scope of the standard twelve lead which could be used by a clinician to improve patient management, and have proved their ability to provide an accurate diagnosis in instances where the standard twelve lead was equivocal.

The use of isointegral maps and discriminant function analysis rose from a need to speed the processing of body surface map information, reduce the data storage requirements of recordings and provide ultimately some form of automated diagnostic system. The mathematical nature of these isointegrals provides a platform which easily lends itself to the use of computers thereby allowing a diagnostic evaluation in minimal time. This diagnosis takes the form of a statistical discriminant function. Statisticians using discriminant function analysis to analyze isointegral maps are presented with the problem of firstly establishing just how many dimensions are involved with solving the problem. This is necessary in order to choose an appropriate discriminant algorithm. However, due both to the integration with respect to time of the ECG signals and the use of a statistical analysis which ignores the nature of the heart's electrical field, the isointegral maps still fail to provide a diagnosis in many instances.

SUMMARY OF THE INVENTION

It is an object of the present invention to provide an apparatus for body surface mapping which can provide an improved diagnostic capability and is relatively easy to use.

Accordingly, the present invention provides an apparatus for body surface mapping, comprising a plurality of electrodes for attachment to spatially separate locations on a human torso, each electrode being capable of detecting the electrical activity associated with a heartbeat and producing a corresponding voltage, means for sampling the voltages on the electrodes a plurality of times during at least part of a cardiac cycle to produce a like plurality of sets of sampled values, and means for calculating and displaying in graphical form the variation with respect to time of at least one characteristic of the sampled values.

In a preferred embodiment the characteristic, for example the instantaneous overall maximum or minimum of the sampled values, varies in position with respect to time and the calculating and displaying means calculates and displays the said variation in position. Preferably the characteristic is displayed as projections of the trajectory onto two planes perpendicular to each other and to the plane containing the electrodes.

The invention also provides a method of body surface mapping, comprising locating a plurality of electrodes at spatially separate locations on a human torso, each electrode being capable of detecting the electrical activity associated with a heartbeat and producing a corresponding voltage, sampling the voltages on the electrodes a plurality of times during at least part of a cardiac cycle to produce a like plurality of sets of sampled values, and calculating and displaying in graphical form the variation with respect to time of at least one characteristic of the sampled values.

In the context of this specification the "trajectory" of a characteristic means the notional path traced out by that characteristic in a three dimensional space of which two dimensions correspond to mutually perpendicular directions in the plane containing the electrodes and the third dimension is time represented as a third spatial direction perpendicular to the plane containing the electrodes.

BRIEF DESCRIPTION OF THE DRAWINGS

An embodiment of the invention will now be described, by way of example, with reference to the accompanying drawings, in which.

DETAILED DESCRIPTION OF THE INVENTION

Figure 3:
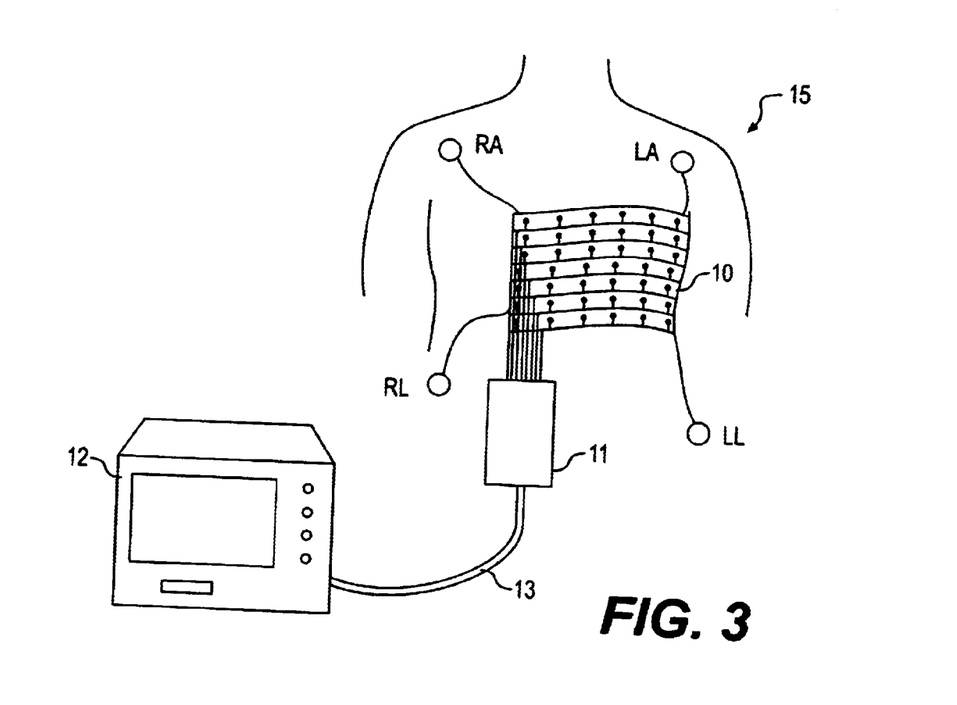
FIG. 3 is a schematic view of the main components of a body mapping apparatus according to the embodiment.

Referring now to the drawings, a body mapping apparatus (FIG. 3) includes a two-dimensional array 10 of a plurality of ECG electrodes removably attachable to a human torso 15. In FIG. 3 the electrodes are shown attached to the anterior surface of the torso but they can extend substantially fully around the torso to provide full body maps of the kind shown in FIG. 2.

The number of electrodes in the array can typically vary from 20 to 100, and in this embodiment it will be assumed there are 80 electrodes. The array 10 also includes right arm (RA), left arm (LA), right leg (RL) and left leg (LL) electrodes and may be constructed as described in International Application Number PCT/IB95/01043.

Each electrode is capable of detecting the electrical activity associated with a heartbeat and producing a corresponding voltage, and it will be appreciated that each electrode in the array 10, although detecting the same component of the heartbeat at any given instant, receives the signal with a different voltage having regard to its different spatial position relative to the heart. Since the electrode signal typically has a strength in millivolts it requires high amplification (>1000) prior to further processing. This is achieved in an interface unit 11 (FIG. 4) which performs front end amplification and analogue to digital data conversion.

Figure 4:
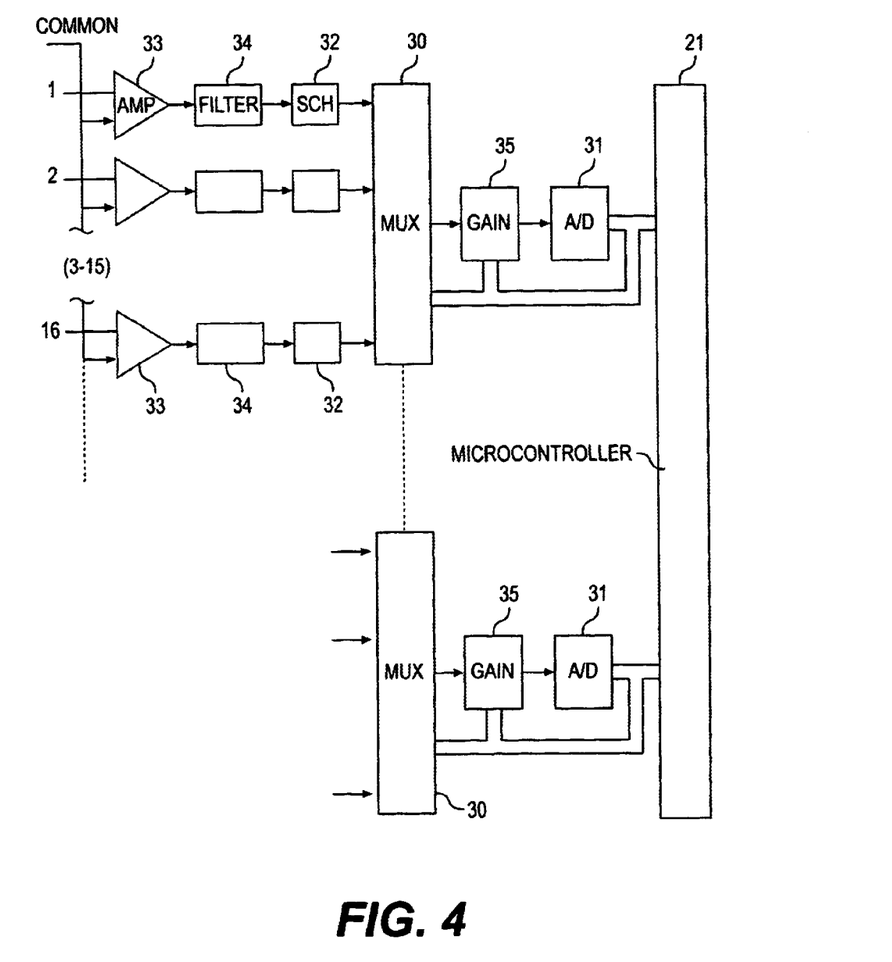
FIG. 4 is a block diagram of the interface unit of FIG. 3.

The individual electrode signals are amplified in respective differential amplifiers 33. The form of amplification employed is described as unipolar since each electrode of the array 10 is referred to a common reference point known as the Wilson central terminal, which is derived from an average of the signals from the limb electrodes RA, LA, RL and LL. These amplifiers 33 buffer the electrode signals with ultra high input impedance (>100M ohms) and high common mode rejection ratios (>80 dB). The amplified signals are then electrically filtered from 0.05–100 Hz in 35 respective filters 34 to further eliminate noise contamination such as DC polarization and low/high frequency radiation and conduction.

Using sample and hold devices 32 the amplified signals from all the electrodes of the array 10 are simultaneously sampled at successive pre-determined instants during at least the QRS period of the cardiac cycle, and the sample values are held during the period (sample/hold period) until the next sampling occurs. In the present embodiment the signals are sampled and held at 1 ms intervals, i.e. at a sampling frequency of 1 KHz. There is no set limit to the sampling frequency required by this invention; however, the greater the frequency the more detailed the subsequent analysis. Preferably the sampling rate is at least 500 Hz.

The total set of signals from the array 10 is divided into five channels of 16 signals per channel. Each channel therefore contains 16 banks of amplification, filtering and sample/hold devices, although only one such channel is shown in full in FIG. 4. A respective 16 to 1 analogue signal multiplexer 30 in each channel is used to sequentially switch through each of the 16 signals during each sample/hold period to enable a single channel digital conversion to be used. Prior to the analog to digital conversion process a programmable gain circuit 35 is employed to allow a selection of common signal gain settings to be chosen by the operator in order to maximize overall signal strength. A microcontroller 21 controls the process of freezing the 16 analogue signals in each channel and during each sample/hold period the analogue multiplexer 30 is selected 16 times with each step sequentially switching one of the 16 signals through to the programmable gain circuit 35 and then into the analogue digital converter 31.

The interface unit 11 therefore produces successive sets of 80 sampled and analog to digital converted signal values, each set having been derived during a respective sample/hold period and therefore constituting a "snapshot" of the electrode voltages at the respective sampling instant. Since the sampling frequency has been assumed to be 1 KHz in this case, 1000 measurements of 80 signals will be produced per second. Although this embodiment shows 16 electrodes per channel, there will typically be from 2 to 20 electrode signals per channel depending upon the total number of electrodes in the array 10.

Figure 5:
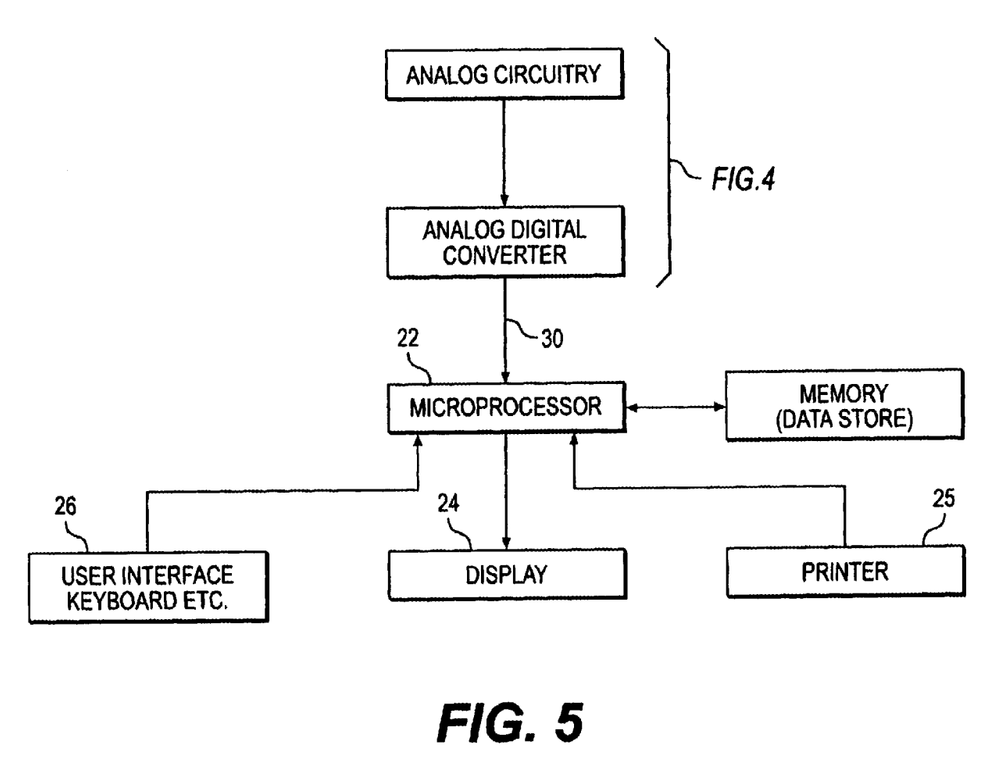
FIG. 5 is a block diagram of the storage, processing and display unit of FIG. 3.

The successive measurements of 80 sampled and analog to digital converted signal values are passed via a direct digital link 13 to a storage, processing and display unit 12 comprising (FIG. 5) a microprocessor 22, a storage device 23, an electronic display device such as a CRT monitor 24, a printer 25 and a user interface such as a keyboard 26. The microprocessor 22 polls each of the channels to transfer sampled data into the storage device 23. In particular, once patient hook-up is satisfactorily completed, the microprocessor 22 stores a pre-selected time frame (typically 5 seconds) of all the channels into the storage device 22. The microprocessor 22 then processes the stored data for display in graphical form on the display screen of the display device 24.

The first step in the processing of the signals stored in the storage device 22 is to determine the 35 "trajectories" of the maximum and minimum sampled values, at least during the heart's QRS (depolarization) period. To explain this concept reference is made to FIG. 6.

Figure 6:
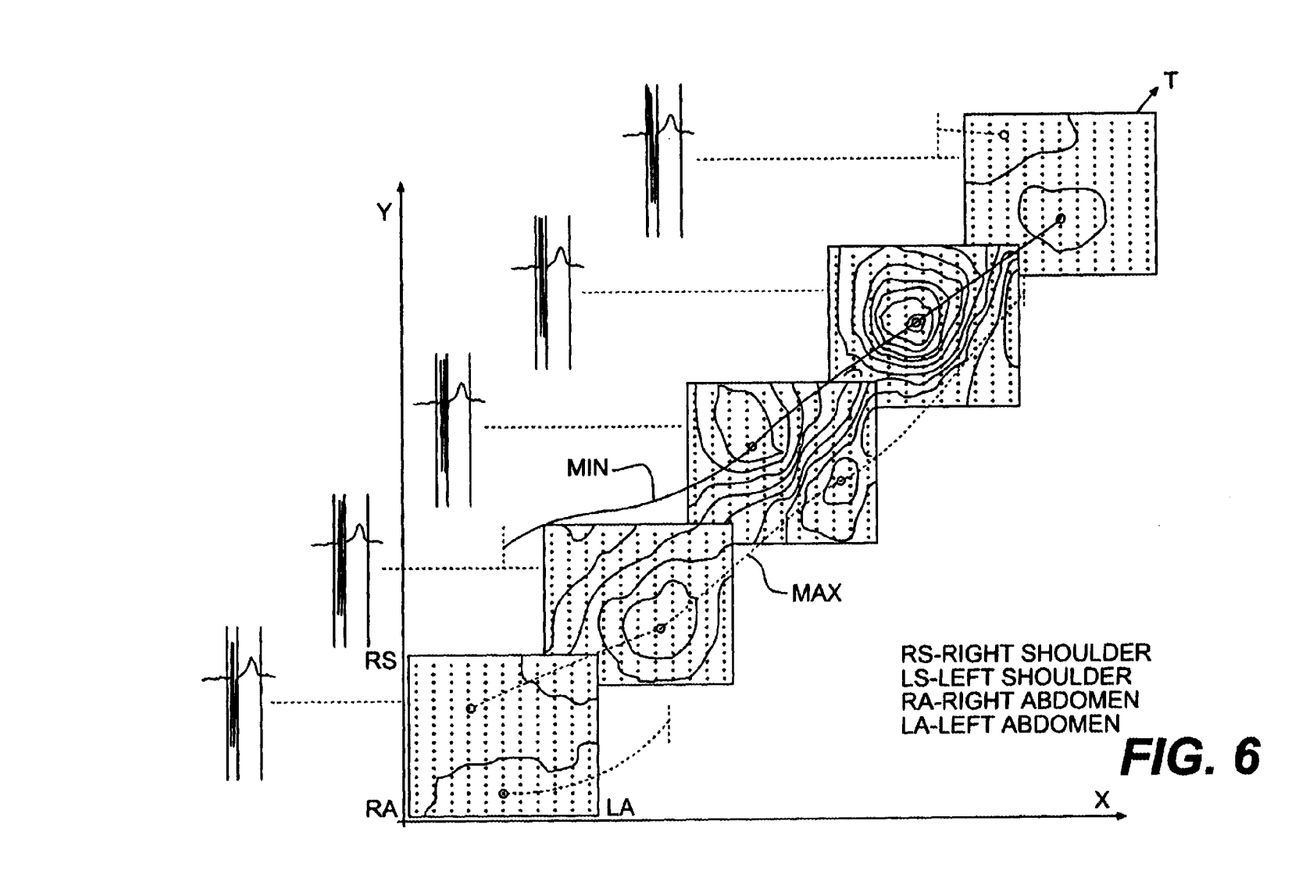
FIG. 6 is a series of isopotential maps notionally produced by the apparatus of FIG. 3.

FIG. 6 shows successive isopotential maps, similar to those shown in FIG. 2, typical of the kind which could be derived from respective successive measurements of 80 sampled signals taken during the heart's depolarization period. It is to be understood that such maps need not actually be produced as such; they are simply presented here for explanation. Each map shows the isopotentials derived in respect of a respective single measurement of 80 samples taken at a particular instant during the heart's depolarization period. Of course, since sampling is effected at 1 KHz in this embodiment, FIG. 6 shows only a small selection of the maps which could be derived.

It will be understood that each map in FIG. 6 corresponds to the electrodes in the array 10 being "unwrapped" from the torso and disposed in a flat plane defined by the x-y axes indicated, the successive maps being disposed along a third spatial axis representing time so that as one progresses from bottom left to upper right in FIG. 6 these represent maps derived from successively later instants of time during the heart's depolarization period. Further it will be understood that the maps shown in FIG. 6 are of the anterior surface of the torso. However, as mentioned above, they could be full body maps.

The diagnostic capabilities of isopotential maps stems from the spatial relationship of the potentials at the various recording sites. These relationships are characterized by the movement of certain features across the body or around the body as time progresses from one instant to the next during the cardiac cycle. For example, on FIG. 6 this is indicated by the lines MAX and MIN which respectively connect the instantaneous maximum and minimum electrode voltages from one map to the next. Similar lines could be drawn connecting preselected electrode voltages between the maximum and minimum, for example the zero volt level.

Such features (maximum and/or minimum and/or preselected voltage) can thus be regarded as taking a "trajectory" in three dimensional space of which two dimensions correspond to x and y directions in the plane containing the unwrapped electrodes and the third dimension is time represented as a third spatial direction perpendicular to the x and y directions.

Figure 7:
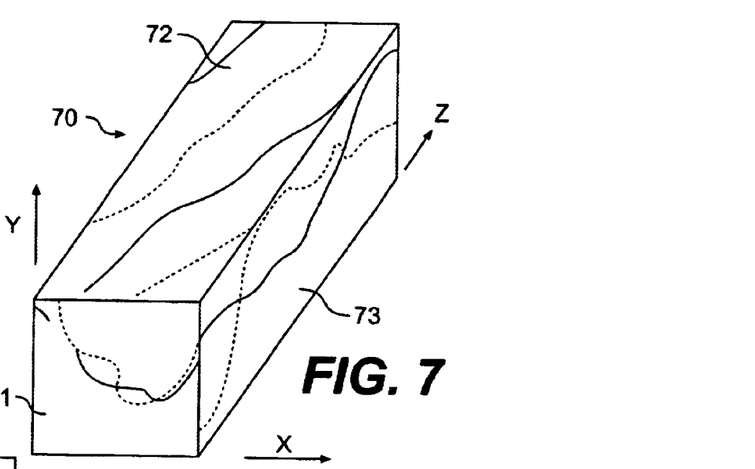
FIG. 7 shows the trajectories of the instantaneous maximum and minimum sampled electrode voltages in three dimensional space.

This three-dimensional space is represented in FIG. 7 by the elongated rectilinear block 70, which conceptually can be regarded as very many densely spaced maps stacked one behind the other in the t direction (spaced at 1 ms intervals in this embodiment). In FIG. 7, the x direction represents the direction generally across or (in the case of full body mapping) around the torso in a horizontal plane, and the y direction represents height. Since three dimensional trajectories cannot adequately be shown in a two dimensional drawing, the trajectories of the instantaneous maximum and minimum electrode voltages are represented in FIG. 8 by their projections onto (a) the x-y plane 71, (b) the plane 72 perpendicular to the plane 71 and parallel to the x-axis, and (c) the plane 73 perpendicular to the plane 71 and parallel to the y-axis.

Referring back to FIG. 5, the microprocessor 22 extracts from the data stored in the storage device 23 (using conventional automatic heartbeat detection means, not shown) the electrode voltage information relating to the period under consideration, i.e. the heart's depolarization period, and calculates the trajectories of the instantaneous maximum and minimum electrode voltages, and/or the trajectory of a preselected electrode voltage such as the zero voltage level, in three dimensional x,y,t space. However, just as the trajectories cannot adequately be shown in a two-dimensional drawing likewise they cannot adequately be shown on the two dimensional display area of the display device 24, and furthermore it is not easy to make a diagnosis from three dimensional trajectories.

Thus, in the preferred embodiment, the microprocessor 22 causes the trajectories to be displayed on the display device 24 as the three projected views shown in FIG. 7, in other words in the form shown in FIG. 8 where (a) is the projected view on the plane 71 containing the electrodes, (b) is the projected view on the plane 72, and (c) is the projected view on the plane 73. As before, although only the projections of the instantaneous maximum and minimum electrode voltages are shown, the trajectory of any preselected electrode voltage level can also or alternatively be shown. These three views may be displayed simultaneously on the display device 24 or they may be called up individually as required by the operator. As an alternative to using an electronic display device 24 the three projected views could be displayed on a chart recorder or graphics printer.

Figure 8A:
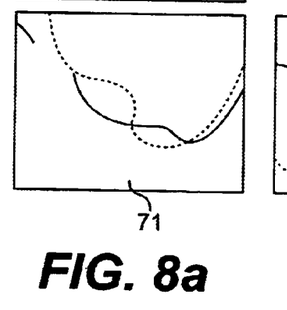
FIG. 8 shows the trajectories resolved into three two-dimensional planes.
Figure 8B:
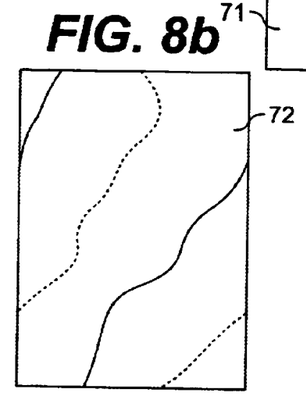
Figure 8C:
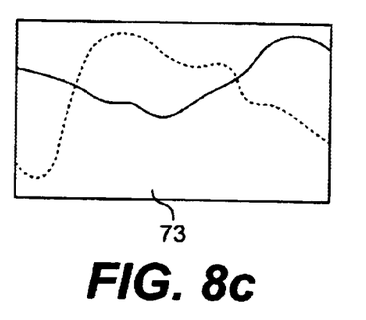

It will be understood that the algorithm used by the microprocessor 22 to produce the three projected views is quite simple, and well within the ability of a person skilled in the art. Each sampled and digitized electrode voltage stored in the storage device 23 will have x, y and t coordinates, x and y being the position of the respective electrode within the array 10 and t being the time of sampling. FIG. 8(a) is therefore just the x,y coordinates plotted onto a plane, FIG. 8(b) is the x,t coordinates plotted onto a plane, and FIG. 8(c) is the y,t coordinates plotted onto a plane.

Figure 8D:
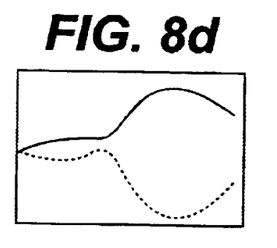

FIG. 8(d) also shows a fourth view which can also be derived by the microprocessor 22 and displayed on the display device 24. The fourth view shows the variation in the absolute values of the instantaneous maximum and minimum voltages as time progresses throughout depolarization. In FIG. 8(d), the horizontal direction represents time and the vertical direction represents voltage amplitude.

These four views can be considered as an individual's body map "signature". It should be appreciated, however, that further such signatures could be presented for other map feature variations throughout the duration of a given cardiac event period (for e.g. repolarization or ST interval etc.).

The trajectory signatures are a representation of the characteristics of the electrical field surrounding a given subject's heart as it activates over time. A disruption of this ordered activation or an abnormal change in field strength at a specific location has the effect of warping some trajectory paths. Which trajectory is warped depends on when the disruption occurs during the cardiac cycle and how it re-shapes the electrical field at each time instant. The trajectory display technique described above accentuates these disruptions in a manner which displays clear group distinction, providing enhanced ability to detect and localize disruptions such as ischaemia and infarction. In fact the homogeneity displayed by subjects from a common group is such that subjects with different cardiac conditions can be distinctly differentiated from each other.

In order to establish how these trajectory signatures bend or warp with different conditions it is possible to collect trajectories from a common group diagnosis together, to form a single trajectory core for the group. The circumference of this core (tunnel) then represents the group boundaries, which completely encompass all trajectories belonging to the group. The name "tunnel" stems from the similarity between this group boundary and the walls of a tunnel into which each trajectory can be fired.

Once the tunnels have been constructed for each group, a diagnosis can be made by simply comparing a single trajectory signature's shape to the shape of the constructed tunnels and selecting either the tunnel which completely encloses the trajectory or in cases where the trajectory does not stay entirely within the walls of the tunnel, selecting the tunnel which most closely matches the trajectory. The comparison can be made using a computer which takes a measure of the distance between a trajectory and the walls of all the tunnels at each time instant and returning an index for each tunnel. The highest index would then be returned by the tunnel which the trajectory is inside the most often and therefore represents the machine's diagnosis. Although the foregoing has described the invention primarily in terms of an embodiment where positional variations of the instantaneous maximum and minimum electrode voltages with time are displayed in graphical form, the invention is applicable to any measurable characteristic of the electrode voltages which changes over time. For example, the possibility of displaying the trajectory of a predetermined electrode voltage level such as the zero volt level has already been discussed.

However, it is also possible to display in graphical form, in the manner shown in FIGS. 8(a) to 8(c), the positional variation of an instantaneous local maximum or minimum of the sampled electrode voltages, indicative of a pseudopod (it will be understood that the minimum and maximum shown in FIGS. 7 and 8 are the overall or major maximum and minimum).

Further, the invention is not limited to the graphical display of positional changes. Thus, for example, the graphical display of the variation in the absolute values of the instantaneous overall maximum and minimum voltages as time progresses throughout depolarization has already been described, FIG. 8(d), and the same can be done for local maxima and minima. It is also possible to display in graphical form the instantaneous rate of change of position with time of the overall or local maximum or minimum, i.e. the instantaneous gradient of the trajectories shown in FIGS. 7 and 8, or the instantaneous rate of change of position with time of a sampled electrode voltage of a predetermined value.

It should also be pointed out that while the manner of graphical presentation at present preferred is in the form of projections such as are shown in FIG. 8, other graphical presentations may be used provided the variation of the relevant characteristic over time is shown. For example, the trajectories could be displayed passing through selected isopotential maps in the manner shown in FIG. 6.

A major advantage of the invention is that the graphical presentation of the positional or other variation of the chosen characteristic with time gives more useful information to the clinician than a single isopotential or isointegral map, and can be much more rapidly produced than a large number of successive maps which would otherwise be needed to convey the same information. This is especially important in time-critical emergency situations. For example, if the apparatus is used in an ambulance the data defining the trajectories can be rapidly transmitted to a hospital for reconstruction of the graphs ahead of the ambulance arrival, so that time is not lost when the patient arrives. At present it is not practically possible to transmit a large number of complete isopotential maps to the hospital ahead of the ambulance.

The invention is not limited by or to the specific embodiments described which can undergo considerable variation without departing from the scope of the invention.

Having thus described at least one illustrative embodiment of the invention, various alterations, modifications, and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. An apparatus for body surface mapping, comprising:
    a two-dimensional array of at least 20 electrodes for attachment to spatially separate locations on a human torso, each electrode being capable of detecting the electrical activity associated with a heartbeat and producing a corresponding voltage,
    means for sampling the voltages on the electrodes a plurality of times during at least part of a cardiac cycle to produce a like plurality of sets of sampled values, and
    means for calculating and displaying in graphical form the variation in position with respect to time of at least one morphological feature of the isopotential maps represented by the plurality of sets of sampled values,
    wherein the at least one morphological feature is displayed as a projection of a trajectory of the morphological feature onto at least one plane perpendicular to a plane containing the electrodes.

2. An apparatus as claimed in claim 1, wherein the morphological feature is the instantaneous overall maximum or minimum of the sampled values.

3. An apparatus as claimed in claim 1, wherein the morphological feature is an instantaneous local maximum or minimum of the sampled values.

4. An apparatus as claimed in claim 1, wherein the morphological feature is a sampled value of a pre-determined level.

5. An apparatus as claimed in claim 1, wherein the morphological feature is displayed as projections of the trajectory onto two planes perpendicular to each other and to the plane containing the electrodes.

6. An apparatus as claimed in claim 1, wherein the electrodes are sampled at a frequency of at least 500 Hz.

7. A method of diagnosing a condition of the human heart comprising:
    locating a two-dimensional array of at least 20 electrodes at spatially separate locations on a human torso, each electrode being capable of detecting the electrical activity associated with a heartbeat and producing a corresponding voltage,
    sampling the voltages on the electrodes a plurality of times during at least part of a cardiac cycle to produce a like plurality of sets of sampled values, the plurality of sets of sampled values being sufficiently large as to allow determination of a trajectory of at least one morphological feature of the isopotential maps represented by the plurality of sets of sampled values,
    calculating and displaying in graphical form the trajectory of the at least one morphological feature, and
    making said diagnosis from the graphical display so produced.

8. The method according to claim 7, wherein the trajectory of the morphological feature is displayed as a projection of the trajectory onto at least one plane perpendicular to a plane containing the electrodes.

9. The method according to claim 8, wherein the trajectory of the morphological feature is displayed as projections of the trajectory onto two planes perpendicular to each other and to the plane containing the electrodes.

10. The method according to claim 7, wherein the morphological feature is the instantaneous overall maximum or minimum of the sampled values.

11. The method according to claim 7, wherein the morphological feature is an instantaneous local maximum or minimum of the sampled values.

12. The method according to claim 7, wherein the morphological feature is a sampled value of a pre-determined level.

13. The method according to claim 7, wherein the electrodes are sampled at a frequency of at least 500 Hz.

14. A method of body surface mapping, comprising:
    locating a two-dimensional array of at least 20 electrodes at spatially separate locations on a human torso, each electrode being capable of detecting the electrical activity associated with a heartbeat and producing a corresponding voltage,
    sampling the voltages on the electrodes a plurality of times during at least part of a cardiac cycle to produce a like plurality of sets of sampled values, and
    calculating and displaying in graphical form the variation in position with respect to time of at least one morphological feature of the isopotential maps represented by the plurality of sets of sampled values, wherein the at least one morphological feature is displayed as a projection of a trajectory of the morphological feature onto at least one plane perpendicular to a plane containing the electrodes.

* * * * *